United States Patent
Yamaguchi

(10) Patent No.: US 10,076,426 B2
(45) Date of Patent: Sep. 18, 2018

(54) STENT AND STENT DELIVERY SYSTEM

(71) Applicant: Terumo Kabushiki Kaisha, Shibuya-ku (JP)

(72) Inventor: Hiroshi Yamaguchi, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 276 days.

(21) Appl. No.: 14/019,816

(22) Filed: Sep. 6, 2013

(65) Prior Publication Data

US 2014/0012361 A1 Jan. 9, 2014

Related U.S. Application Data

(63) Continuation of application No. PCT/JP2012/055227, filed on Mar. 1, 2012.

(30) Foreign Application Priority Data

Mar. 25, 2011 (JP) .................. 2011-68401

(51) Int. Cl.
*A61F 2/95* (2013.01)
*A61F 2/958* (2013.01)
(Continued)

(52) U.S. Cl.
CPC ............ *A61F 2/82* (2013.01); *A61F 2/915* (2013.01); *A61F 2/958* (2013.01); *A61F 2002/91566* (2013.01); *A61F 2230/0013* (2013.01)

(58) Field of Classification Search
CPC .. A61F 2/958; A61F 2/82; A61F 2/915; A61F 2230/0013; A61F 2002/91508–2002/91583
(Continued)

(56) References Cited

U.S. PATENT DOCUMENTS 5,843,175 A * 12/1998 Frantzen ............... 623/1.15
5,895,406 A * 4/1999 Gray ................... A61F 2/91
606/198

(Continued)

FOREIGN PATENT DOCUMENTS

JP 2003-520055 A 7/2003
JP 2007-526096 A 9/2007
(Continued)

OTHER PUBLICATIONS

International Search Report (PCT/ISA/210) dated Apr. 10, 2012, by the Japanese Patent Office as the International Searching Authority for International Application No. PCT/JP2012/055227.

*Primary Examiner* — Christopher L Templeton
*Assistant Examiner* — George J Ulsh
(74) *Attorney, Agent, or Firm* — Buchanan Ingersoll & Rooney PC

(57) ABSTRACT

A stent and a stent delivery system are configured to exhibit good slip strength, flexibility, and expandability. The stent includes a plurality of wave-shaped struts positioned at intervals in the circumferential direction of the stent, and a plurality of connecting struts positioned between the wave-shaped struts. Each of the wave-shaped struts extends from one end to the other end in the axial direction, and has proximate portions that form portions in the vicinity of an adjacent wave-shaped strut, distant portions that form portions away from the adjacent wave-shaped strut, and straight portions that connect the proximate portions and the distant portions. The straight portions extend in the circumferential direction of the stent in a state in which the stent is mounted on the balloon. The connecting struts connect to each other the distant portions of adjacent wave-shaped struts.

22 Claims, 7 Drawing Sheets

INITIAL STATE

(51) Int. Cl.
*A61F 2/915* (2013.01)
*A61F 2/82* (2013.01)

(58) Field of Classification Search
USPC ... 623/1.11, 1.12, 1.16, 1.17, 1.18, 1.19, 1.2
See application file for complete search history.

(56) References Cited

U.S. PATENT DOCUMENTS

| | | | |
|---|---|---|---|
| 6,132,461 A * | 10/2000 | Thompson | A61F 2/91 623/1.15 |
| 2002/0065549 A1 * | 5/2002 | White | A61F 2/91 623/1.15 |
| 2004/0215312 A1 | 10/2004 | Andreas | |
| 2005/0004656 A1 | 1/2005 | Das | |
| 2006/0136037 A1 | 6/2006 | DeBeer et al. | |

FOREIGN PATENT DOCUMENTS

| | | |
|---|---|---|
| JP | 2008-516668 A | 5/2008 |
| JP | 2009-240796 A | 10/2009 |
| WO | WO 2006/044147 A2 | 4/2006 |

* cited by examiner

EXPANDED STATE

STENT AND STENT DELIVERY SYSTEM

CROSS REFERENCES TO RELATED APPLICATIONS

This application is a continuation of International Application No. PCT/JP2012/055227 filed on Mar. 1, 2012, and claims priority to Japanese Application No. 2011-068401 filed on Mar. 25, 2011, the entire content of both of which is incorporated herein by reference.

TECHNICAL FIELD

The present invention generally relates to a stent and a stent delivery system.

BACKGROUND DISCUSSION

A stent delivery system, which is a medical device used to improve a stenosis or occlusion generated in the lumen in vivo, is provided with a dilatable balloon positioned on the outer periphery of the distal portion of a hollow shaft portion, and a stent positioned on the outer periphery of the balloon and having wave-shaped struts that are expanded by the dilatation of the balloon. After reaching a target region (stenosis or occlusion), the stent, which is mounted on the balloon by caulking with its diameter being reduced, is plastically deformed by the dilatation of the balloon and is indwelled in a state of being in close contact with the inner surface of the target region.

The wave-shaped struts of a conventional stent extend in the circumferential direction of the stent and are multiply positioned at intervals in the axial direction of the stent, each of the wave-shaped struts including proximate portions that form portions in the vicinity of an adjacent wave-shaped strut, distant portions that form portions away from the adjacent wave-shaped strut, and straight portions that connect the proximate and distant portions. The proximate portions of adjacent wave-shaped struts are connected by connecting portions.

Since the straight portions of the wave-shaped strut extend in the axial direction of the stent in a state in which the stent is mounted on the balloon, the above-described stent has the problem of being prone to slip along the axial direction of the balloon. The entire stent also has the problem of insufficient flexibility (compliance with the curvature of the lumen in vivo) due to a large difference in stiffness between the wave-shaped struts and the connecting portions.

In view of the improvement in flexibility, extension of the wave-shaped struts in the axial direction of the stent may, for example, reduce the difference in stiffness in the axial direction of the stent (for example, see Japanese PCT National Publication No. 2008-516668, the contents of which are hereby incorporated by reference.)

However, since the proximate portions of adjacent wave-shaped struts in the stent described in Japanese PCT National Publication No. 2008-516668 are directly connected to each other, the proximate portions are hardly deformed even if the stent is expanded by a balloon, and thus the stent may not be expanded well.

SUMMARY

An aspect of the disclosure here involves a stent mounted on an outer periphery of a dilatable balloon and configured to be expanded by dilatation of the balloon, the stent including a plurality of wave-shaped struts positioned at intervals in a circumferential direction of the stent, and a plurality of connecting struts positioned between the wave-shaped struts. Each of the wave-shaped struts extends from one end to the other end in an axial direction of the stent, and has proximate portions that form portions in the vicinity of an adjacent wave-shaped strut, distant portions that form portions away from the adjacent wave-shaped strut, and straight portions that connect the proximate and distant portions. The straight portions extend in the circumferential direction of the stent in a state in which the stent is mounted on the balloon, and the connecting struts connect the distant portions of the adjacent wave-shaped struts to each other.

Another aspect of the disclosure involves a stent delivery system that includes a balloon catheter having a hollow shaft portion and a dilatable balloon positioned on an outer periphery of a distal portion of the shaft portion, and the stent mounted on the balloon and configured to be expanded by the dilatation of the balloon.

According to the disclosure here, the wave-shaped struts, which extend from one end to the other end in the axial direction of the stent, reduce a difference in stiffness in the axial direction of the stent, and improve flexibility of the entire stent. The straight portions of the wave-shaped strut, which extend in the circumferential direction in a state in which the stent is mounted on the balloon, suppress the occurrence of a slip of the stent along the axial direction relative to the balloon. In addition, since the distant portions of adjacent wave-shaped struts are connected indirectly through the connecting struts, the adjacent straight portions or the adjacent proximate portions in the axial direction of each of the wave-shaped struts hardly come into contact with each other when the balloon is dilated, and the stent is expanded well. Thus, a stent and a stent delivery system having good slip strength, flexibility, and expandability can be provided.

The connecting struts preferably extend straight in the circumferential direction of the stent. In this case, slippage of the stent along the axial direction relative to the balloon can be more reliably suppressed. The distant portions connected by the connecting struts are preferably disposed at one end and/or the other end of the stent. Hence, since the connecting struts extending in the circumferential direction of the stent are located at the ends of the stent and a separation of the ends of the stent from the balloon decreases, the occurrence of the ends of the stent curling away from the balloon is suppressed while passing through a path to a target region.

The connecting strut is preferably connected in the center of each of the distant portions with respect to the axial direction of the stent, and only parts of the distant portions are more preferably connected by the connecting struts. With respect to the axial direction of the stent, the length of the distant portion connected by the connecting strut is particularly preferably greater than the length of the distant portion that is not connected by the connecting strut. In this case, the distant portions in addition to the proximate portions are easily deformed based on the dilatation of the balloon, and thus the stent is more easily expanded.

The straight portion is preferably extended such that a crossing angle relative to the axial direction of the stent is 45 degrees or more and 90 degrees or less, more preferably the crossing angle is 60 degrees or more and 90 degrees or less, and particularly more preferably the crossing angle is 90 degrees. In this case, the occurrence of a slip of the stent along the axial direction relative to the balloon can be more effectively suppressed.

The stent and a stent delivery system disclosed here exhibits good slip strength, flexibility, and expandability.

Other features, characteristics and aspects of the stent and a stent delivery system will become apparent from the following detailed description considered with reference to the accompanying drawings.

BRIEF DESCRIPTION OF THE DRAWINGS

The accompanying drawings are included in the specification and form a part of the disclosure here, and are used to disclose aspects and principles of the disclosure here together with the detailed description set forth below.

DETAILED DESCRIPTION

Figure 1:
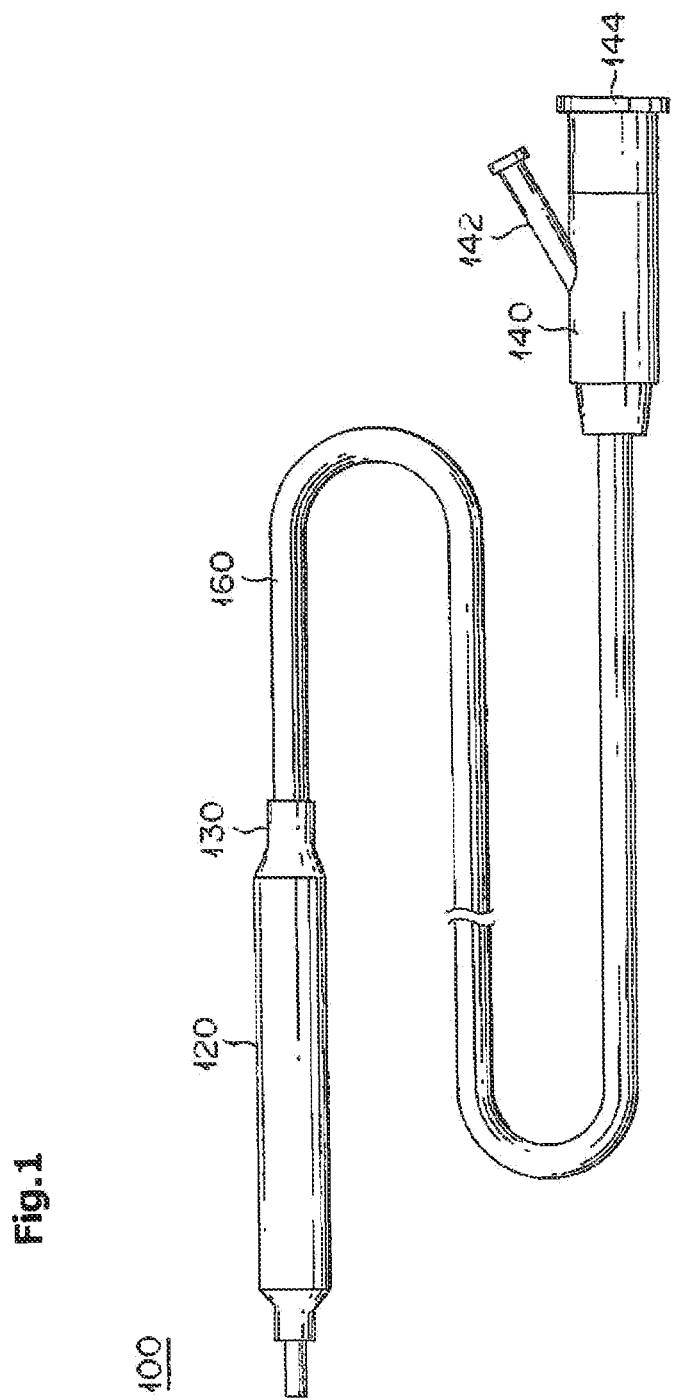
FIG. 1 is a schematic view illustrating a stent delivery system according to one exemplary embodiment of the disclosure herein.
Figure 2:
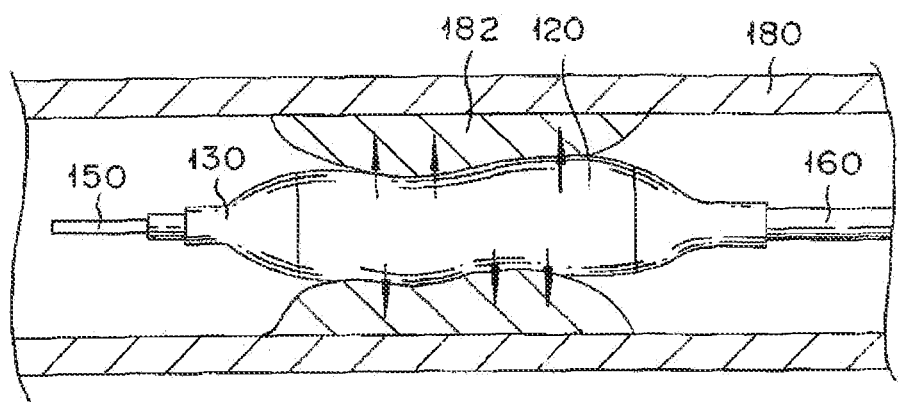
FIG. 2 is a schematic view illustrating the use of the stent delivery system.

As illustrated in FIG. 1, a stent delivery system 100 according to one embodiment disclosed by way of example, which is used to improve a stenosis (or occlusion) 182 in a lumen 180 in vivo (see FIG. 2), includes a hollow shaft tube (shaft portion) 160, a balloon 130 positioned on the outer periphery of the distal portion of the shaft tube 160, a stent 120 mounted on the balloon 130, and a hub 140 located at the proximal end of the shaft tube 160.

The lumen 180 in vivo is, for example, a coronary artery of the heart, and one of the purposes of indwelling the stent 120 is to prevent restenosis after percutaneous transluminal coronary angioplasty (PTCA).

The stent 120, which is mounted on the outer periphery of the balloon 130, has a good "slip strength", "flexibility" and "expandability". With respect to stent 120, "slip strength" means that there is sufficient difficulty in the occurrence of a slip along the axial direction of the stent relative to the balloon, "flexibility" means that there is compliance with the curvature of the lumen 180, and "expandability" means the ease of expansion by the dilatation of the balloon. The stent 120 is used to maintain the patency of the lumen 180 by being indwelled on the inner surface of the stenosis 182 in close contact therewith.

The balloon 130, which is dilatable, is configured to expand the stent 120 mounted on the outer periphery thereof to increase its diameter. The stent 120 is mounted on the balloon 130 by caulking (engaging) with its diameter in a reduced state, and this thereby suppresses slip of the stent 120 relative to the balloon 130 and its "peeling" (i.e., separation) away from the balloon 130.

The hub 140 has an injection port 142 and a guide wire port 144. The injection port 142 is used, for example, to introduce and discharge pressurized fluid to dilate the balloon 130. The pressurized fluid is a liquid such as saline or an angiographic contrast agent. The guide wire port 144 is used to insert a guide wire 150 into the shaft tube 160 to protrude the guide wire 150 beyond the distal end portion of the shaft tube 160.

The stent 120 is indwelled, for example, in the following manner:

The distal end portion of the stent delivery system 100 is first inserted into the lumen 180 of a patient, and is positioned at the stenosis 182, i.e. a target region, with the guide wire 150 therein that has already been protruded in advance beyond the distal end portion of the shaft tube 160. Introducing the pressurized fluid through the injection port 142 then dilates the balloon 130, and causes the expansion and plastic deformation of the stent 120 to bring the stent 120 into close contact with the stenosis 182 (see FIG. 2). The balloon 130 is next depressurized to release the engagement between the stent 120 and the balloon 130, and the stent 120 is separated from the balloon 130. The stent 120 is thus indwelled in the stenosis 182 while being plastically deformed. The stent delivery system 100, from which the stent 120 has been separated, is finally moved backward and removed from the lumen 180.

One skilled in the art will appreciate that the stent delivery system 100 is not limited to the disclosed embodiment as being applied to a stenosis generated in a coronary artery of the heart, and that the stent delivery system 100 can also be applied to a stenosis generated in other blood vessels, bile duct, trachea, esophagus, urethra and the like.

The distal portion of the stent delivery system 100 will now be described in detail.

Figure 3:
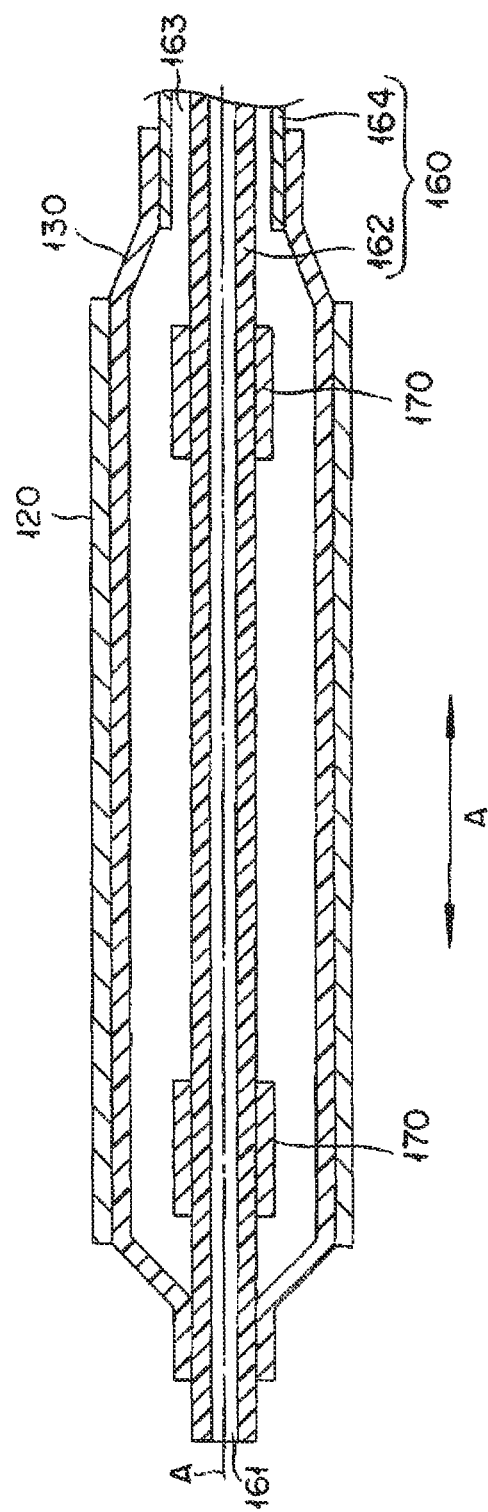
FIG. 3 is a sectional view illustrating a distal portion of the stent delivery system illustrated in FIG. 1.

FIG. 3 is a sectional view illustrating the distal portion of the stent delivery system illustrated in FIG. 1.

The balloon 130 is positioned on the outer periphery of the distal portion of the shaft tube 160 along its axial direction A in a folded state (or contracted state), and is dilatable. Since the stent 120 is mounted on the outer periphery of the balloon 130, strut bodies 122 (shown in FIG. 4) of the stent 120 are expanded by the dilatation of the balloon 130.

The material forming the balloon 130 is preferably one of those having flexibility, such as polyolefin, polyvinyl chloride, polyamide, polyamide elastomer, polyurethane, polyesters such as polyethylene terephthalate, polyarylene sulfide such as polyphenylene sulfide, silicone rubber, and latex rubber. Examples of the polyolefin include polyethylene, polypropylene, ethylene-propylene copolymer, ethylene-vinyl acetate copolymer, and cross-linked ethylene-vinyl acetate copolymer.

The stent 120 is made of a biocompatible material. Examples of the biocompatible material include nickel-titanium alloy, cobalt-chromium alloy, stainless steel, iron, titanium, aluminum, tin, and zinc-tungsten alloy.

The shaft tube 160 includes an inner tube 162 and an outer tube 164 into which the inner tube 162 is inserted. The inner tube 162, which is in communication with the guide wire port 144 of the hub 140, extends through the balloon 130 to a distal end. Thus, the guide wire 150 inserted into the guide wire port 144 is protrudable beyond the distal end of the stent delivery system 100, and the interior of the inner tube 162 constitutes a lumen 161 for the guide wire.

The outer periphery of the inner tube 162, disposed within the interior of the balloon 130 as shown in FIG. 3, is provided with cylindrical markers 170. The cylindrical markers 170, which are made of a radiopaque material, provide a clear angiogram under X-ray fluoroscopy, and thus allow the positions of the balloon 130 and the stent 120 to be easily confirmed. Examples of the radiopaque material include platinum, gold, tungsten, iridium, and an alloy thereof.

The outer tube 164 is disposed outside the inner tube 162. A lumen 163, which is defined by a space between the inner peripheral surface of the outer tube 164 and the outer peripheral surface of the inner tube 162, is in communication with the injection port 142 of the hub 140. The balloon 130 is fixed in a liquid-tight manner on the outer periphery of the distal end portion of the outer tube 164, and the interior of the balloon 130 is in communication with the lumen 163. Thus, the pressurized fluid introduced from the injection port 142 passes through the lumen 163 and is introduced into the balloon 130, thereby allowing the balloon 130 to be dilated. A method of fixing the balloon 130 to the outer periphery of the distal end portion of the outer tube 164 is not particularly limited, and for example, an adhesive or heat-sealing may be applied thereto.

The material constituting the outer tube 164 is preferably one having flexibility, for example, polyolefins such as polyethylene, polypropylene, polybutene, ethylene-propylene copolymer, ethylene-vinyl acetate copolymer, ionomer, a mixture of two or more of these, thermoplastic resin such as soft polyvinyl chloride resin, polyamide, polyamide elastomer, polyester, polyester elastomer, polyurethane, fluorine resin, silicone rubber, and latex rubber.

The material constituting the inner tube 162 may be the same material as the outer tube 164 or a metallic material. The metallic material may be, for example, stainless steel or Ni—Ti alloy.

In addition, the material constituting the hub 140 (see FIG. 1) may be, for example, thermoplastic resin such as polycarbonate, polyamide, polysulfone, polyarylate, and methacrylate-butylene-styrene copolymer.

The stent 120 will now be described in detail.

Figure 4:
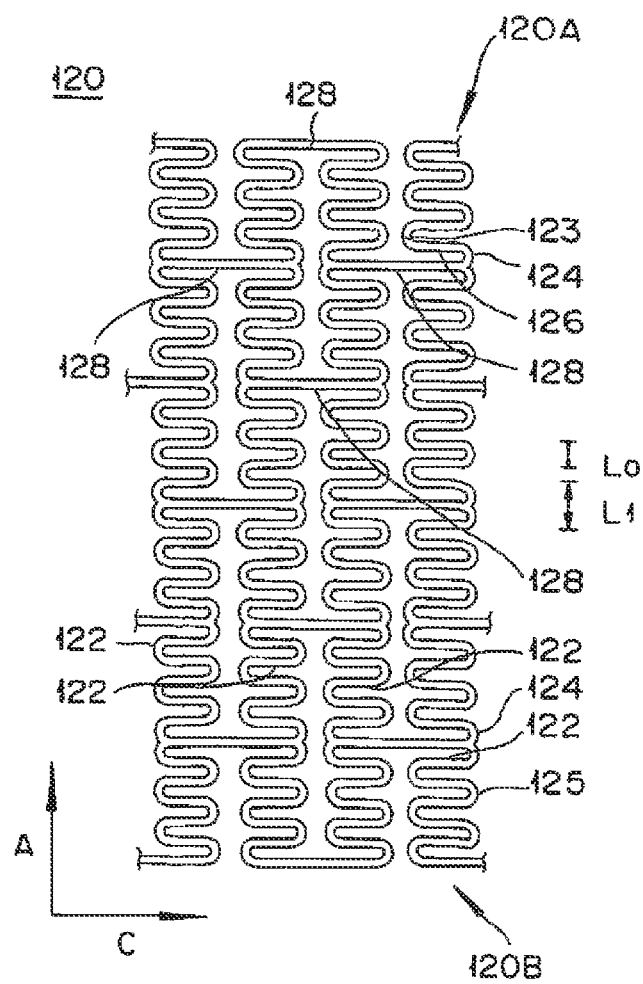
FIG. 4 is a developed view illustrating an initial state of the stent illustrated in FIG. 3.
Figure 5:
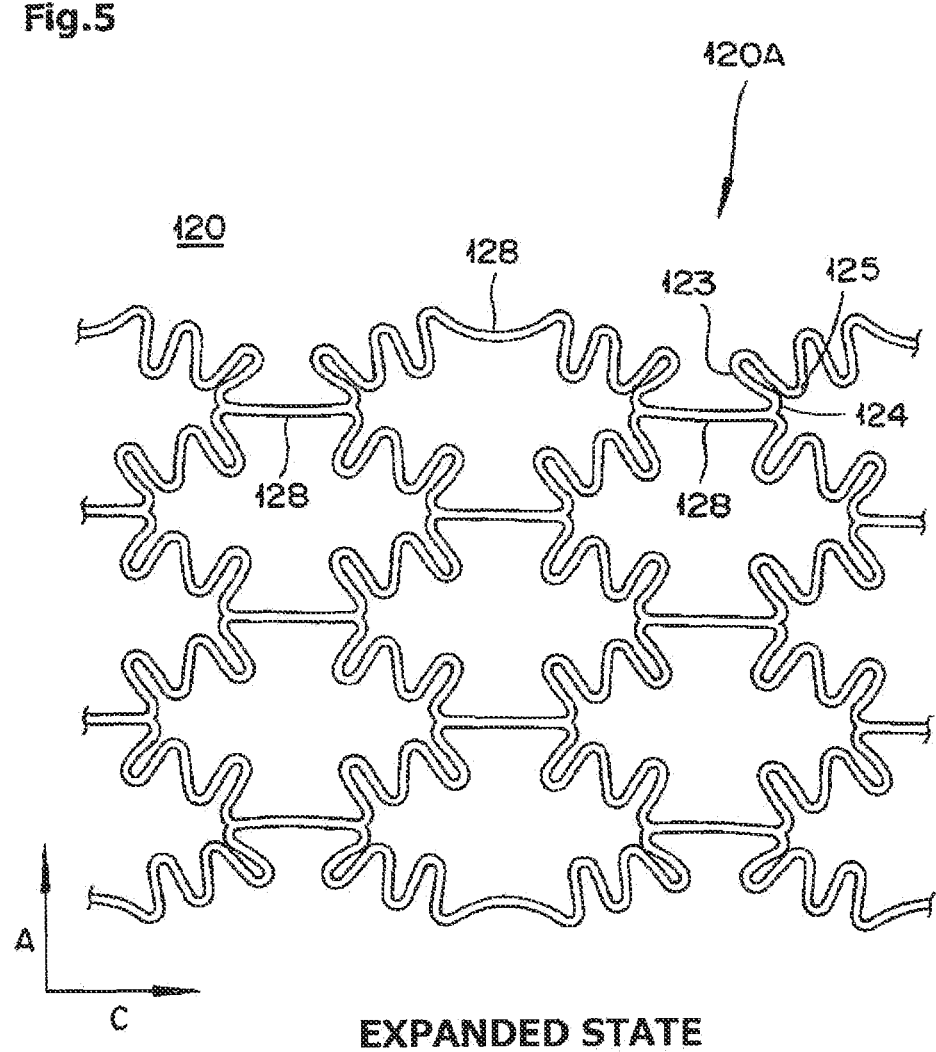
FIG. 5 is a developed view illustrating an expanded state of the stent.
Figure 6:
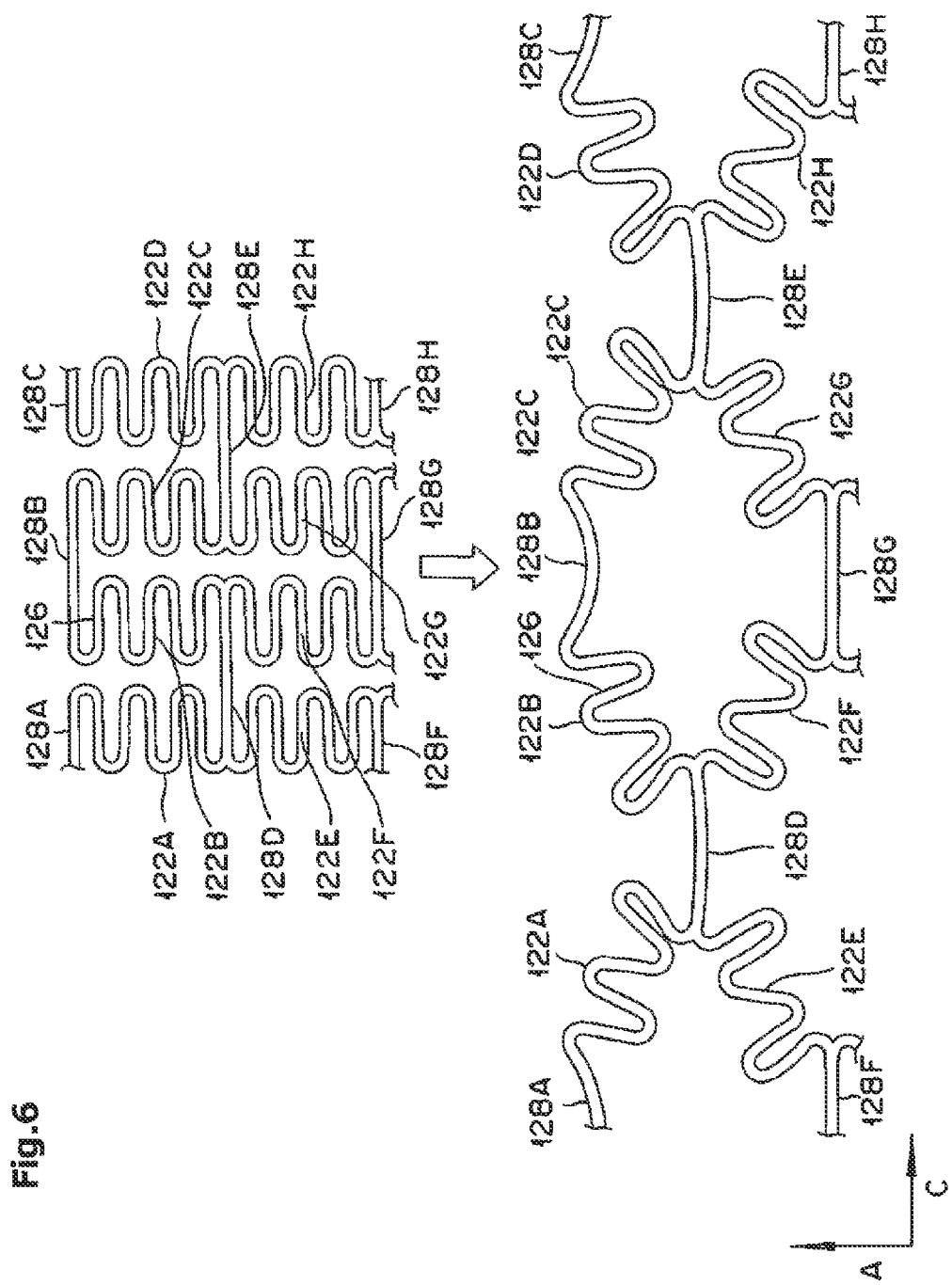
FIG. 6 is an explanatory view illustrating the deformation of the stent from the initial state to the expanded state.

FIG. 4 is a developed view illustrating an initial state of the stent illustrated in FIG. 3. FIG. 5 is a developed view illustrating an expanded state of the stent. FIG. 6 is an explanatory view illustrating the deformation of the stent from the initial state to the expanded state.

In a state (initial state) of being mounted on the balloon 130, the stent 120 includes, as illustrated in FIG. 4, a plurality of wave-shaped strut bodies (wave-shaped struts) 122 positioned at intervals in the circumferential direction C, and a plurality of connecting struts 128 positioned between the strut bodies 122. The strut bodies 122 extend from one end 120A to the other end 120B in the axial direction A, each of the strut bodies 122 having proximate portions 123, distant portions 124, 125 and straight portions 126.

The proximate portions 123 and the distant portions 124, 125 are portions that are in the vicinity of and away from an adjacent strut body 122, respectively. The straight portions 126 connect the proximate portions 123 with the distant portions 124, 125 and extend in the circumferential direction C. The proximate portions 123 and the distant portions 124, 125, which are turning portions of the straight portions 126, have curved (bent) shapes.

The connecting strut 128 extends straight in the circumferential direction C, and connects the distant portions 124 of adjacent strut bodies 122 to each other. Thus, the strut bodies 122 and the connecting struts 128 constitute an annular body as a unit. Note that the proximate portions 123 of adjacent strut bodies 122 are not connected to each other at all.

As described above, the strut bodies 122 extend from the one end 120A to the other end 120B in the axial direction A. This reduces the difference in stiffness in the axial direction A, and improves flexibility of the entire stent 120.

The straight portions 126 of the strut body 122, which as described above extend in the circumferential direction C in a state in which the stent 120 is mounted on the balloon 130, suppress the occurrence of slippage of the stent 120 along the axial direction A relative to the balloon 130 such that it exhibits good slip strength. This inhibits the stent 120 from dropping-off of the balloon 130, for example, while the distal end portion of the stent delivery system 100 passes through a stenosis.

Since the distant portions 124 of adjacent strut bodies 122 are indirectly connected to each other via the connecting struts 128, the straight portions 126 and the proximate portions 123 that are adjacent in the axial direction A of each of the strut bodies 122 have minimal contact and thus do not interfere with each other when the balloon 130 is dilated. As a result, the stent 120 expands well.

The distant portions 124 connected by the straight connecting struts 128 are disposed at the one end 120A and the other end 120B of the stent. That is, since the connecting struts 128 extending straight in the circumferential direction C are located at the ends of the stent, separation (curling) away from the balloon 130 decreases. The occurrence of curling away from the balloon 130 at the ends of the stent is thus suppressed while passing through a path to a target region. For example, difficulty when the distal end portion of the stent delivery system 100 passes through bent and meandering blood vessels is reduced. A risk that the stent 120 is caught, for example, in the stenosis 182 and drops off is also reduced.

This configuration is also advantageous to manufacture the stent delivery system 100: The occurrence of curling away from the balloon 130 at the ends of the stent is suppressed when the stent 120 is mounted on the balloon 130. The distant portions 124 connected by the connecting struts 128 may be disposed only at the one end 120A of the stent, if necessary.

The connecting struts 128 connect only part of the distant portions 124 (connected to every third portion in the configuration illustrated in FIG. 4), and the strut body 122 has the distant portions 125 that are not connected by the connecting struts 128. Accordingly, the distant portions 125 that are not connected by the connecting struts 128, in addition to the proximate portions 123, are also easily deformed by the dilatation of the balloon 130 and thus the stent is easily expanded.

The connecting strut 128 is connected to the center of the distant portion 124 with respect to the axial direction A, and a length L1 of the distant portion 124 connected by the connecting strut 128 is greater than a length L0 of the distant portion 125 that is not connected by the connecting strut 128. Accordingly, the distant portions 124 connected by the connecting struts 128 are also deformed by the dilatation of the balloon 130, and thus the stent is easily expanded.

The connection position of the connecting strut 128 is not limited to the center. The ratio between the respective lengths L1 and L0 of the distant portions 124 and 125 is not particularly limited, but preferably in the range of L0:L1=1: 1.5 to 1:4.0. The shape of the connecting strut 128 is not limited to being straight, and it may also have a bent or wavy shape.

In order to effectively suppress the occurrence of a slip of the stent 120 along the axial direction A relative to the balloon 130, the straight portion 126 and the connecting strut 128 are preferably extended such that a crossing angle relative to the axial direction A is 45 degrees or more and 90 degrees or less, i.e., between 45-90 degrees, and more preferably the crossing angle is 60 degrees or more and 90 degrees or less, i.e., between 60-90 degrees, and particularly more preferably the crossing angle is 90 degrees.

When the stent 120 is indwelled on, for example, the inner surface of the stenosis 182 in close contact therewith, the stent 120 is expanded (its diameter is increased) by the dilatation of the balloon, and the shape changes from the shape illustrated in FIG. 4 to the shape illustrated in FIG. 5.

In this case, the expansion direction is consistent with the extending direction of the connecting struts 128, while the expansion direction intersects the extending direction of the proximate portions 123 and the distant portions 124 of the strut body 122. Therefore, the connecting struts 128 are difficult to deform, but the proximate portions 123 and the distant portions 124 are easily deformed. Also, as shown in FIG. 5, the straight portions 126 and the proximate portions 123 adjacent in the axial direction A minimally contact or interfere with each other when they are expanded by the balloon.

More specifically, as illustrated in FIG. 6, the shapes of the connecting struts 128 (128A to 128H) before and after the expansion are nearly the same and without significant change, while the strut bodies 122 (122A to 122H) disposed between the connecting struts 128, which strut bodies 122 include the proximate portions 123, the distant portions 124, 125 and the straight portions 126, are significantly distorted and, for example, the straight portions 126 become inclined in the axial direction A. As a result, the length in the axial direction A of the stent 120 is reduced according to the amount of expansion of the stent diameter. Whether the entire stent 120 can be expanded uniformly may be studied using, for example, the finite element method (FEM).

Figure 7:
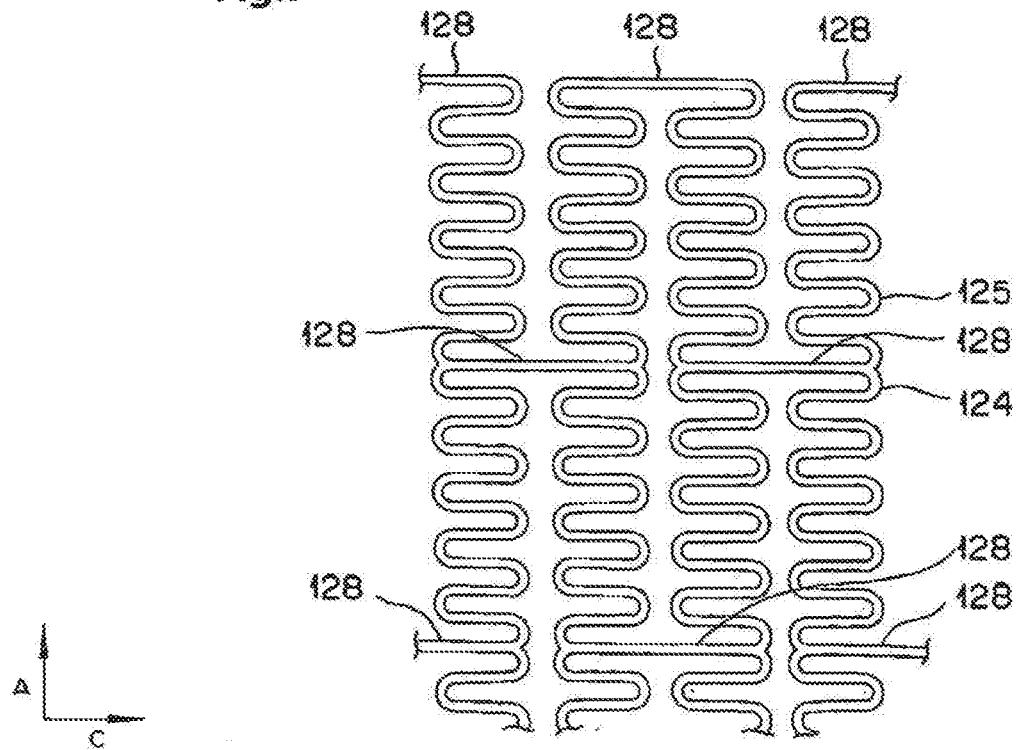
FIG. 7 is a developed view illustrating a first modification according to another embodiment of the disclosure here.
Figure 8:
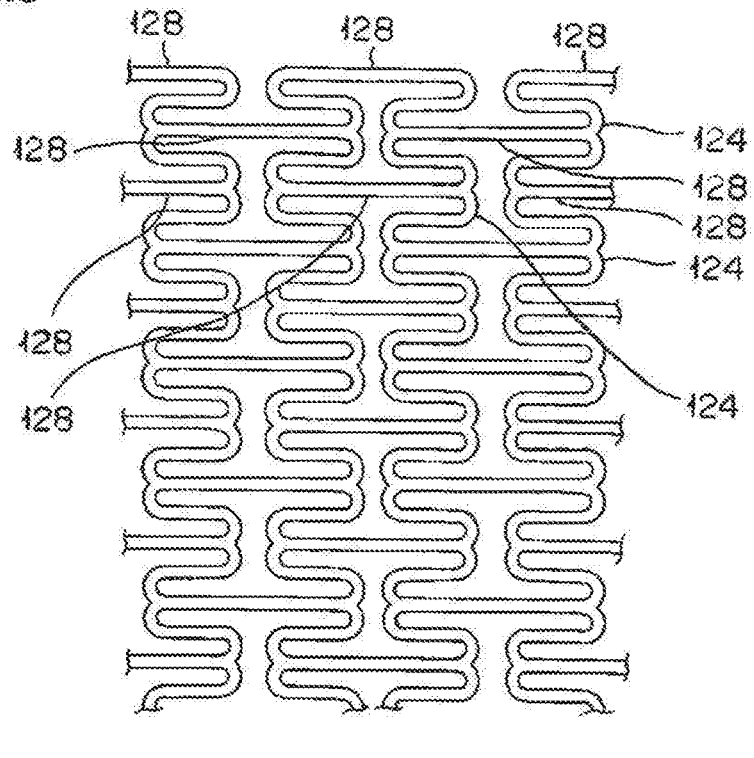
FIG. 8 is a developed view illustrating a second modification according to a further embodiment of the disclosure here.

FIGS. 7 and 8 are developed views illustrating first and second modifications according to further embodiments of the disclosure, respectively.

The position of connection between the distant portions 124 using the connecting struts 128 is not limited to every third distant portion illustrated in FIG. 4. For example, the connecting struts 128 may connect every fifth distant portion 124 (see FIG. 7) or all the distant portions 124 (see FIG. 8).

A method of forming the strut body 122 and the connecting strut 128 is not particularly limited. For example, based on a strut pattern, e.g., the patterns of the strut body 122 and the connecting strut 128, the strut body 122 and the connecting strut 128 may be formed by laser-cutting the outer periphery of a stent material, or by placing a masking material corresponding to the strut pattern on the outer periphery of the stent material and performing etching.

According to the exemplary embodiments as described above, a stent and a stent delivery system having good slip strength, flexibility, and expandability can thus be provided.

The disclosure here is not limited to the above-described exemplary embodiments, and may be variously modified within the scope of the claims. For example, a balloon catheter is not limited to the over-the-wire (OTW) type, and the rapid exchange (RX) type may also be applied thereto.

The stent may be made of a biodegradable polymer that is decomposed and absorbed over time in vivo, or may be coated on its surface with a drug such as a physiologically active substance. The biodegradable polymer is, for example, polylactic acid, polyglycolic acid, or copolymer of lactic acid and glycolic acid. The physiologically active substance is, for example, an anti-cancer agent, immunosuppressive agent, antibiotics, or antithrombotics. Furthermore, the marker may be positioned on the proximal side of the shaft tube.

The detailed description above describes a stent and stent delivery system disclosed by way of example. The disclosure is not limited, however, to the precise embodiment and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent mountable on an outer periphery of a dilatable balloon and expandable by dilatation of the balloon, the stent comprising:
a plurality of wave-shaped struts positioned at intervals in a circumferential direction of the stent; and
a plurality of connecting struts positioned between the wave-shaped struts, wherein each of the wave-shaped struts extends from one end to an other end in an axial direction of the stent,
wherein at least one of the plurality of connecting struts is disposed at the one end, and wherein at least one of the plurality of connecting struts is disposed at the other end in the axial direction of the stent,
wherein each of the wave-shaped struts includes a plurality of proximate portions that form portions in the vicinity of an adjacent wave-shaped strut, a plurality of distant portions that form portions further away from the adjacent wave-shaped strut than the plurality of proximate portions, and a plurality of straight portions that connect the proximate and distant portions,
wherein at least one of the plurality of connecting struts is disposed between adjacent ones of the plurality of proximate portions,
wherein each of the plurality of connecting struts has a length greater than a length of each of the plurality of straight portions; and
wherein, when the stent is mounted on the balloon, the straight portions extend in the circumferential direction of the stent and the connecting struts connect distant portions of adjacent ones of the wave-shaped struts to each other.

2. The stent according to claim 1, wherein
the connecting struts extend straight in the circumferential direction of the stent.

3. The stent according to claim 1, wherein
each of the wave-shaped struts has one of the plurality of distant portions positioned at the one end and/or the other end of the stent, and
the distant portions positioned at the one end and/or the other end of the adjacent wave-shaped strut are connected to each other by the at least one of the plurality of connecting struts.

4. The stent according to claim 1, wherein
the at least one of the plurality of connecting struts is connected to a center of each of the distant portions with respect to the axial direction of the stent.

5. The stent according to claim 1, wherein
only some of the plurality of distant portions are connected by the connecting struts, and each of the wave-shaped struts also has some of the plurality of distant portions that are not connected by the connecting struts.

6. The stent according to claim 5, wherein,
with respect to the axial direction of the stent, a length of one of the distant portions connected by the at least one of the plurality of connecting struts is greater than a length of one of the distant portions that is not connected by the connecting strut.

7. The stent according to claim 1, wherein each of the plurality of straight portions is extended such that a crossing angle relative to the axial direction of the stent is between 45 degrees and 90 degrees.

8. The stent according to claim 7, wherein each of the plurality of straight portions is extended such that a crossing angle relative to the axial direction of the stent is between 60 degrees and 90 degrees.

9. The stent according to claim 8, wherein each of the plurality of straight portions is extended such that a crossing angle relative to the axial direction of the stent is 90 degrees.

10. The stent according to claim 1, wherein the plurality of proximate portions of adjacent wave-shaped struts are not connected to each other.

11. The stent according to claim 1, wherein a distance between adjacent said distant portions is greater than a distance between adjacent said proximate portions.

12. A stent delivery system comprising:
a balloon catheter including a hollow shaft portion and a dilatable balloon positioned on an outer periphery of a distal portion of the shaft portion;
a stent mounted on the balloon and configured to be expanded by the dilatation of the balloon;
said stent comprising:
a plurality of wave-shaped struts positioned at intervals in a circumferential direction of the stent; and
a plurality of connecting struts positioned between the wave-shaped struts,
wherein each of the wave-shaped struts extends from one end to an other end in an axial direction of the stent,
wherein at least one of the plurality of connecting struts is disposed at the one end, and wherein at least one of the plurality of connecting struts is disposed at the other end in the axial direction of the stent,
wherein each of the wave-shaped struts includes a plurality of proximate portions that form portions in the vicinity of an adjacent wave-shaped strut, a plurality of distant portions that form portions further away from the adjacent wave-shaped strut than the plurality of proximate portions, and a plurality of straight portions that connect the proximate and distant portions,
wherein at least one of the plurality of connecting struts is disposed between adjacent ones of the plurality of proximate portions,
wherein each of the plurality of connecting struts has a length greater than a length of each of the plurality of straight portions; and
wherein, when the stent is mounted on the balloon, the straight portions extend in the circumferential direction of the stent and the connecting struts connect the distant portions of adjacent wave-shaped struts to each other.

13. The stent delivery system according to claim 12, wherein the connecting struts extend straight in the circumferential direction of the stent.

14. The stent delivery system according to claim 12, wherein each of the wave-shaped struts has one of the plurality of distant portions positioned at the one end and/or the other end of the stent, and the distant portions positioned at the one end and/or the other end of the adjacent wave-shaped strut are connected to each other by the at least one of the plurality of connecting struts.

15. The stent delivery system according to claim 12, wherein the at least one of the plurality of connecting struts is connected to a center of each of the distant portions with respect to the axial direction of the stent.

16. The stent delivery system according to claim 12, wherein only some of the plurality of distant portions are connected by the connecting struts, and each of the wave-shaped struts also has some of the plurality of distant portions that are not connected by the connecting struts.

17. The stent according to claim 16, wherein, with respect to the axial direction of the stent, a length of one of the distant portions connected by the at least one of the plurality of connecting struts is greater than a length of one of the distant portions that is not connected by the connecting strut.

18. The stent delivery system according to claim 12, wherein each of the plurality of straight portions is extended such that a crossing angle relative to the axial direction of the stent is between 45 degrees and 90 degrees.

19. The stent delivery system according to claim 18, wherein each of the plurality of straight portions is extended such that a crossing angle relative to the axial direction of the stent is between 60 degrees and 90 degrees.

20. The stent delivery system according to claim 19, wherein each of the plurality of straight portions is extended such that a crossing angle relative to the axial direction of the stent is 90 degrees.

21. The stent delivery system according to claim 12, wherein the plurality of proximate portions of adjacent wave-shaped struts are not connected to each other.

22. The stent delivery system according to claim 12, wherein a distance between adjacent said distant portions is greater than a distance between adjacent said proximate portions.

* * * * *